United States Patent [19]

Silva et al.

[11] 4,008,714
[45] Feb. 22, 1977

[54] BRAIN WAVE CORRELATION SYSTEM AND METHOD OF DELIVERING A RECORDED PROGRAM OF MATERIAL EDUCATIONAL IN CONTENT

[76] Inventors: Jose R. Silva; John M. Narrace, both of P.O. Box 1149, Laredo, Tex. 78040

[22] Filed: Feb. 4, 1976

[21] Appl. No.: 655,666

Related U.S. Application Data

[63] Continuation of Ser. No. 490,262, July 22, 1974, abandoned, which is a continuation-in-part of Ser. No. 334,743, Feb. 22, 1973, Pat. No. 3,875,930.

[52] U.S. Cl. ............................. 128/2.1 B; 35/8 A; 35/22 R
[51] Int. Cl.[2] ......................................... A61B 5/04
[58] Field of Search ......... 128/2.1 B, 2.1 M, 2.1 R, 128/2.1 Z; 35/22 R, 8 A

[56] References Cited

UNITED STATES PATENTS

| 3,846,831 | 11/1974 | Johnson, Jr. et al. ............... 35/8 A |
| 3,855,998 | 12/1974 | Hildalgo-Briceno ............ 128/2.1 B |
| 3,896,790 | 7/1975 | Dikmen .......................... 128/2.1 B |

OTHER PUBLICATIONS

Stockman, "Proceedings of the Institute of Radio Engineers," Jan. 1951, p. 160.

Primary Examiner—William E. Kamm
Attorney, Agent, or Firm—Bard, Springs & Jackson

[57] ABSTRACT

Methods and apparatus are provided for deriving an audible indication of a person's brain wave frequency, and for actuating a tape player or the like to deliver a recorded program of material educational in content when said frequency reaches a preselected frequency value or range. Means may also be included for rendering the audible indication of the measured frequency of the subject person inaudible upon actuation of said tape player.

11 Claims, 2 Drawing Figures

4,008,714

BRAIN WAVE CORRELATION SYSTEM AND METHOD OF DELIVERING A RECORDED PROGRAM OF MATERIAL EDUCATIONAL IN CONTENT

RELATED CASES

This application is a continuation of our prior copending Application Ser. No. 490,262, filed July 22, 1974, and now abandoned, which in turn is a continuation-in-part of prior coending Application Ser. No. 334,743, filed Feb. 22, 1973, and which is now U.S. Pat. No. 3,875,930, issued Apr. 8, 1975.

BACKGROUND OF INVENTION

This invention relates to methods and apparatus for measuring and correlating physiological and psychological performances of human subjects and the like, and more particularly relates to methods and apparatus for measuring and correlating the brain wave frequency of a human subject with a preselected frequency sought to be attained.

It is well known that the human brain generates electrical pulsations at frequencies which are functionally related to mental and physical condition, and it is now well known that there are certain definite frequency ranges wherein the mental activity and capability of a person differs to a distinguishable degree. More particularly, the human brain provides pulsations in the "Beta Range" (above 14 cps) when a person is "wide awake" and in a normally active state, and that the frequency is in the "Delta Range" (below 4 cps) when the person is in a deep sleep or coma condition. When the brain wave frequency drops to zero, of course, the person is physiologically and mentally dead.

Between these two frequencies is the "Alpha Range", wherein the frequency rate falls between 7–14 cps, and the "Theta Range," wherein the rate is between 4–7 cps. The existence and significance of these ranges have only recently been recognized and are not fully understood, since no two human beings ever react exactly the same. It is now clearly apparent that when a person's brainwave frequencies are within the Alpha range, that a person is often imbued with significantly greater powers of concentration and a deeper inner awareness, and frequently with an enhanced capacity for such powers as extrasensory perception and the like. Relatively little experimentation has been done with regard to the Theta range, but subjects have sometimes exhibited extraordinary capabilities when in that state.

It was previously thought that a person's brain wave frequency is a completely uncontrollable condition, and that a person tends to drift between Beta and Delta in an entirely involuntary manner. For this reason, established scientific and medical opinion has, until recently, tended to look with skepticism on claims advanced on behalf of esoteric practices such as yogi, transcendental mediation, etc. Now, however, conditioning exercises have been devised and made available whereby an experienced practitioner of otherwise ordinary capacities can shift his brain wave frequency rate into the Alpha range to obtain benefits such as those hereinbefore mentioned. Since these conditioning exercises are formulated and based on accepted scientific theory rather than on the more philosophical and metaphysical beliefs adhered to by practitioners of yoga and transcendental mediation, and since the effects obtained by such exercises are repeatable to a much greater degree, they are now widely accepted in conventional scientific circles.

Insofar as the measurement of human brain waves is concerned, it is old and well known as evidenced by U.S. Pat. Nos. 3,662,746 and 3,623,477, to derive and electroencephalographical voltage signal indicative of such waves or pulsations. This signal may be visually or even audibly displayed, or it may be graphically recorded to provide what is popularly known as an "EEG." Thus, conventional detection and recording apparatus is used to monitor the subject using the aforementioned conditioning exercises, in order to establish when and if the subject actually enters the Alpha state. For example, see the December 1972 issue of *Electronics World*, pp 33–38, and also U.S. Pat. No. 3,548,812, for a fuller discussion of experimentation utilizing such measurements. See also U.S. Pat. Nos. 2,860,627, 3,662,746, and 3,658,054, for other discussions of contentional apparatus of this type.

The conditioning exercises hereinbefore referred to are comprised of a series of predetermined mental images which the subject or practitioner formulates according to prescribed sequence, and no external agency is actually required as such. Since the practitioner seldom if ever experiences any physical sensation when shifting to the Alpha state, some users of the exercises have practiced the technique while connected to electroencephalographic apparatus in order to indicate that the Alpha state has in fact been attained, as indicated in the aforementioned article in *Electronics World*. Further, in some cases the encephalographic signal has been translated into an audio output, whereby the frequency of the signal will inform and, to a limited extent, guide the practitioner in attaining the Alpha state. This technique is often of advantage in assisting or guiding a practitioner of limited experience and confidence. Nevertheless, the same audible signal which assists and guides the practitioner in descending out of the Beta range is also a disadvantage when the practitioner approaches the Alpha range. A practitioner is not in a hypnotic state when in the Alpha range, of course, and is still fully aware of his surroundings and in complete control of his faculties. Hence, the audible signal is often an unwanted distraction which impedes rather than assist the pactitioner at the very moment he is about to enter the Alpha range.

Because of this disadvantage, it is conventional when utilizing the assistance of the audible representation of the practitioner's brain wave frequency, to employ the assistance of another person to monitor the signal and disconnect it as the practitioner enters the Alpha range. However, this is also undesirable for the obvious reason that the conditioning exercises are designed for self use, and it defeats the entire purpose of the technique if another person is required to be in attendance.

In another aspect, it should be understood that achieving the Alpha level or range is not ordinarily the end sought to be attained, but is merely a pre-condition for the making of various other experiments and the like. In many instances, it is desired to follow entry into the Alpha level by actuating a tape player or the like which will then deliver a recorded program of material which may be educational in content and purpose, or alternatively may be a sequence of selected audible stimuli for the purpose of pschological and parapyschological experimentation.

Obviously, it is at the least an undesirable diversion to the subject practitioner, if he is required to personally and of his own volition actuate the auxiliary device presenting the educational program, stimuli, etc. Even if this function is performed by another person who may be monitoring the experiment or process however, it is not always possible for the assisting person to actuate the auxiliary device at the preferred time, which is the moment of entry into the Alpha state.

These and other disadvantages of the prior art are overcome with the present invention, and novel methods and apparatus are herewith provided for monitoring and assisting the user of such conditioning exercises without the aid and attendance of another party.

SUMMARY OF INVENTION

In an ideal embodiment of the present invention, a conventional headgear-type assembly of electrodes is provided in conjunction with other conventional circuitry for generating a train of electrical pulses or waves in functional relationship to the electrical pulses which are produced by the brain of the wearer of such electrodes. In addition, however, means is further included to provide an audible indication of the rate of occurrence of such pulses. Furthermore, means is also preferably included for the purpose of suppressing this indication of the subject's brain wave frequency characteristic coincident with entry into the Alpha or other level sought to be reached and, coincident with such suppression, activating the tape player or other auxiliary device sought to be used.

In the ideal embodiment of the present invention, the brain wave measurement signal is applied to a triggered oscillator, which is adapted to generate a fixed tone signal, but which interrupts such signal upon the receipt of each wave or pulse in the brain wave signal. Hence, the output of the triggered oscillator will be composed of a sequence of discrete tone bursts, and although the frequency of such bursts is below the normal audio frequency range, the occurrence of such bursts and their rate or frequency will nevertheless be clearly evident to the subject person.

As the practitioner descends through the Beta range, the practitioner will hear the rate of occurrence or frequency of these tone bursts decline until their frequency of occurrence approaches or approximates the preselected frequency which he seeks to attain. In the present invention, however, means is also provided whereby the audio output signal will be suppressed when the rate of tone bursts reaches the rate sought to be attained, and whereby such suppression will continue so long as the two signals remain within a certain preselected range of frequency difference. Coincident with such suppression, a tape player or the like is actuated.

As hereinbefore stated, there is an apparent though not fully understood correlation between a person's physiological and psychological performances, and thus it is often useful to measure and observe one or more such physiological characteristics in conjunction with the use of the conditioning exercises. Ideally, therefore, the apparatus of the present invention may further include a galvanic circuit for correlatively measuring skin resistivity, and for also applying such measurement to the speaker in the form of an audio signal of distinguishable character. Accordingly, means is provided for substituting the output of the galvanic circuit for the encephalic signal primarily used to produce the tone bursts.

It is therefore a feature of the present invention to provide means and method for providing an audible comparison of the rate of occurrence of human brain waves in a form whereby variations in such rate of occurrence may be discernable to the average listener.

It is a further feature of this invention to generate a tone signal, to interrupt such signal as a function of measured human brain waves.

It is another feature of the invention to interrupt an audible tone signal at a rate functionally related to the frequency of human brain waves, and to suppress such audible tone signal when such interruption rate corresponds functionally to a predetermined brain wave within the Alpha range.

It is a further feature of the present invention to correlate the suppression of such tone signal with the activation of an auxilliary means such as a tape player for providing a preselected program of audible information which may be educational in content.

These and other features and advantages of the present invention will become apparent from the following detailed description, wherein reference is made to the figures in the accompanying drawings.

IN THE DRAWINGS

DETAILED DESCRIPTION

Figure 1:
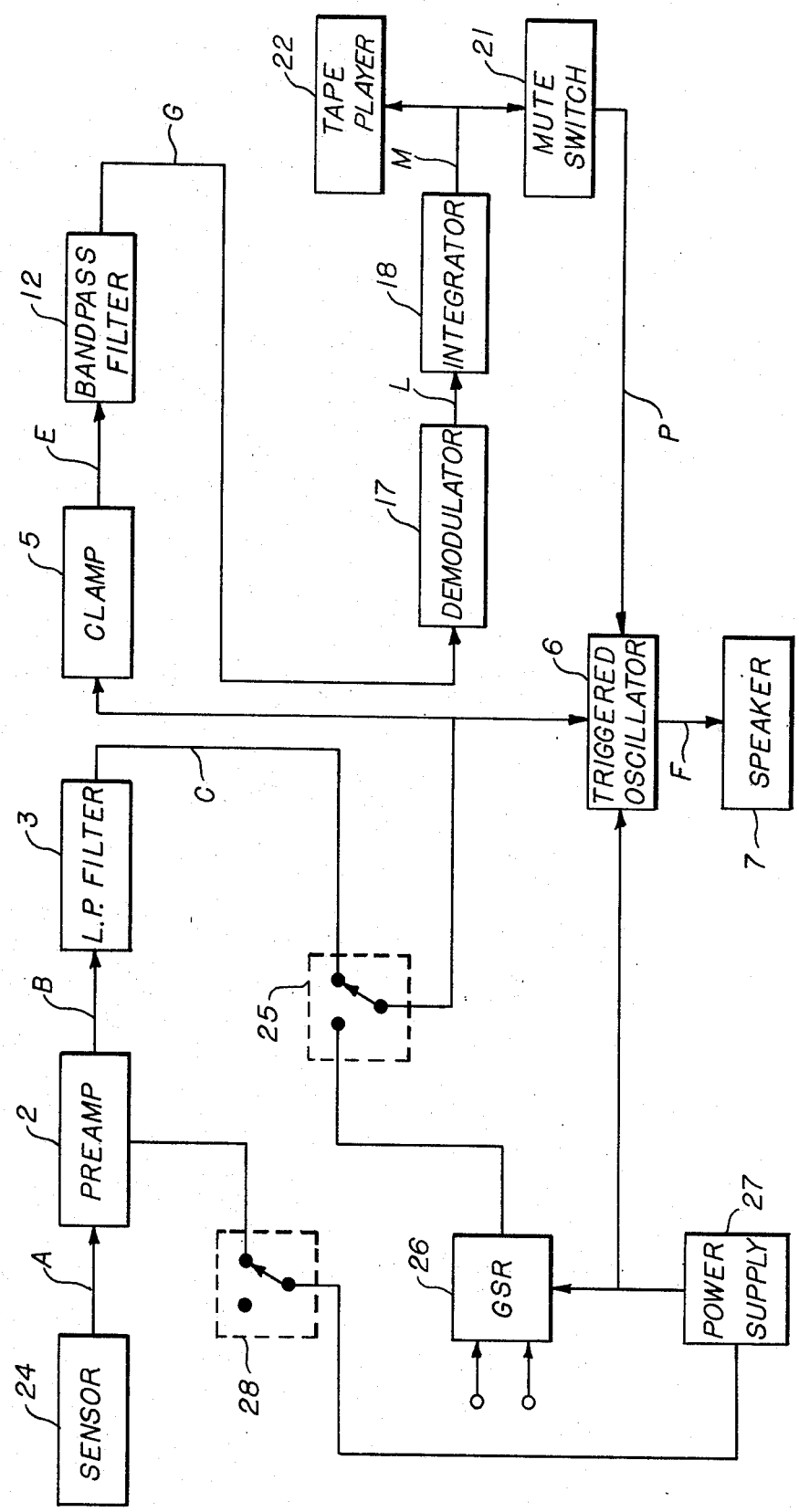
FIG. 1 is a simplified functional diagram of an exemplary form of apparatus embodying and suitable for practicing the concepts of the present invention.

Referring now to FIG. 1, there may be seen a simplified functional representation of a system embodying the concepts of the present invention and basically composed of a monitoring section for producing an audible indication of a person's brain wave frequency, for automatically suppressing such indication when attaining the Alpha frequency or the like, and for actuating a tape player or the like coincident with such suppression. As further indicated in FIG. 1, the system may also include a third section for producing and substituting for such brain wave indication signal a correlative audible indication of another different selected physiological feature of the subject person, such as heart beat, breathing rate, body temperature, skin resistivity or the like.

In particular, the monitoring section may include a suitable brain wave sensor 24 such as that depicted in U.S. Pat. No. 3,658,054, for generating an output signal A which is representative in configuration and frequency of the brain waves produced by the subject person. Since the amplitude of Signal A is relatively extremely low, it is preferably applied to a conventional amplifier 2 which, in turn, produces a functionally related output signal B of a more desirable amplitude.

As hereinbefore indicated, the electrode or sensor 24 operates to detect and conduct brain wave signals produced by the subject person. Signals emanating from the brain are quite small in amplitude, and thus the sensor output signal A, and also the amplified signal B, will often include other unwanted pulses originating from sources in the vicinity or noise in the circuits represented in FIG. 1. Accordingly, signal B is preferably applied to a suitable filter circuit 3 for producing an output signal C which is an amplified representation of the subject's brain waves, but which is also substantially free of other spurious indications.

In some applications of the technique hereinbefore discussed, it is preferred that an audible representation of the subject's brain wave characteristics be provided only when the subject attains the Alpha "level". Accordingly, the filter 3 may conveniently be a low-pass circuit adapted to pass only signals having a frequency less than 14 cps or some other preselected level.

Referring again to FIG. 1, it may be seen that output signal C may be applied to one of the two input terminals of a suitable selector switch 25 having its output terminal coupled to the input of a triggered oscillator 6. The purpose of the triggered oscillator is preferably to generate a constant tone signal of a predetermined audible pitch in response to either the positive or negative portion of each undulation in signal C. Accordingly, it may be seen in FIG. 2 that the output signal F, which may be coupled to a suitable speaker circuit 7, is composed of a sequence of discrete tone signals which occur in functional response to each brain wave signal emitted by the subject person and conveyed by the sensor 24 (unless eliminated by the filter circuit 3).

Referring again to FIG. 1, it may further be seen that the system may also include a third section for measuring and indicating a selected physiological characteristic of the subject person. Accordingly, there may be included a second sensor 26 which may be a simple psychogalvanometer such as the "Lie Detector" Model 28-182 which is manufactured by Allied Radio Shack, and which produces a frequency signal representative of the skin resistivity of the subject. This putput signal may be applied directly to the speaker circuit 7 to provide a third distinguishably different tone signal, but for present purposes it is preferably connected to the other input terminal of the selector switch 25. Thus, whichever input is selected by the selector switch 25, the output of switch 25 will be applied to the aforementioned triggered oscillator 6 which, in turn, will generate a signal F for application to the speaker circuit 7. The system will preferably be provided with a suitable power supply 27, and a suitable on-off switch 28 whereby power can be conveniently connected or disconnected from the system.

As hereinbefore stated, it is a feature of the ideal embodiment of the invention to provide for suppression of the signal F whenever the actual brain wave frequency of the subject approaches or reaches the Alpha range (or some other predetermined frequency). Accordingly, the output signal from the LP filter 3 is preferably coupled through the selector switch 25 to a conventional clamping circuit 5 for producing an appropriate square wave frequency E from signal C which is applied, in turn, to the input side of a bandpass filter 12 preferably having a plurality of different values and means for selecting the same.

Referring again to FIG. 1, it may be seen that the square wave frequency E may conveniently be applied to the input of an appropriate bandpass filter 12, whereby an output signal G will appear only when the input signal E corresponds to the preselected Alpha frequency sought to be attained by the experimenter. As hereinbefore stated, the so-called Alpha level corresponds to a range of different frequencies. On the other hand, although different persons have a tendency to go to different frequencies within that range, there is also a tendency for a person to go to the same frequency each time he projects himself into the Alpha level. Accordingly, the bandpass filter 12 is preferably adjustable to pass a plurality of different frequencies, in order that the circuitry depicted in FIG. 1 may be used by more than one particular experimenter.

Referring again to FIG. 1, it will be seen that the output signal E from the bandpass filter 12 is preferably applied to a demodulator circuit 17 which, in turn, applies an output signal L to the input of a suitable integrator circuit 18. The integrator circuit 18, in turn, produces an output signal M having a form suitable for a gating function, as may be seen in FIG. 2. Accordingly, the output signal M may be used to actuate a tape player 22 or other auxiliary device to deliver a recorded program of material educational in content whenever the value of signal M is greater than "zero" or reference amplitude.

As hereinbefore stated, it is a feature of the present invention to suppress the audible indication of the actual frequency of the subject's brain waves upon achieving the Alpha level sought to be attained. The importance of this feature arises from the fact that alteration of the frequency of one's brain waves often requires rather intense concentration on the part of the subject, and thus it is always desirable to minimize all distraction during the use of the technique, and especially at the point at which the subject attains the level sought to be reached. Accordingly, signal L is preferably applied to a suitable mute switch 21, whereby signal P is generated at the same moment that signal L is applied to the tape player 22.

The purpose of signal P is to inactivate the triggered oscillator 6. Accordingly, it will be apparent that signal F will be suppressed, and that the audible output from the speaker 7 will disappear, at the same instant that the tape player 22 is activated. On the other hand, it will also be apparent that if the subject's brain wave frequency deviates significantly from the setting of the bandpass filter 12, output signal G will disappear, the tape player 22 will thereupon become inactivated, and the speaker 7 will again produce an audible indication.

Figure 2:
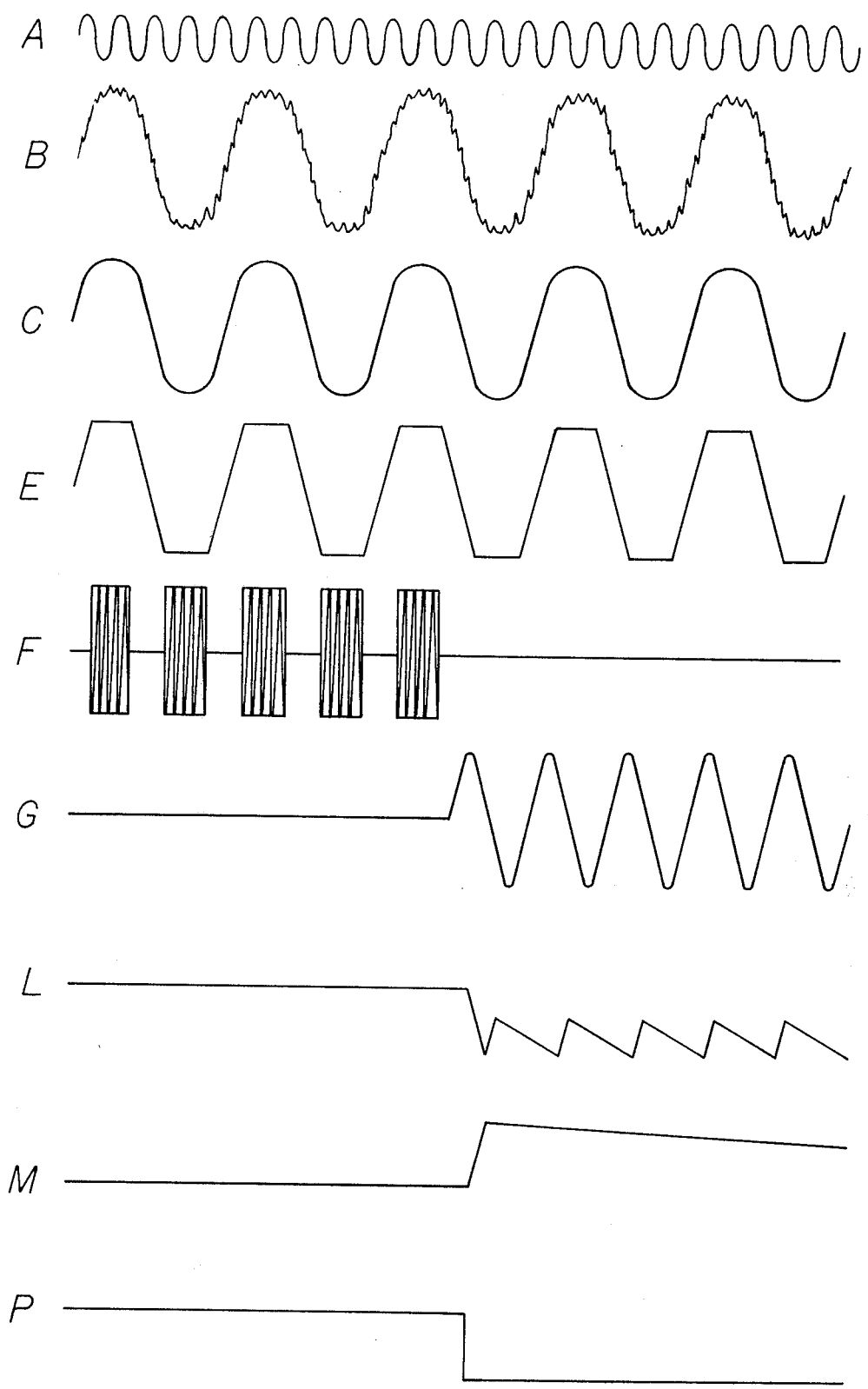
FIG. 2 is a simplified diagrammatic representation of the wave forms of various signals occurring at selected locations throughout the apparatus depicted in FIG. 1.

It should be noted, however, that the tone of the output signal F from the triggered oscillator 6 is of a constant preselected pitch indicative of the source of the signal as hereinbefore stated. Accordingly, and as indicated in FIG. 2, it is the rate of occurrence of each discrete segment or portion of such tone signal, which is representative of the skin resistivity of the subject, rather than the pitch or tone of the signal. In this respect, it should be noted that the frequency or occurence rate of the segments of the signal may be indicated by maintaining a fixed duration of silence between each segment or tone burst of the signal, and by varying the duration of the tone bursts or segments accordingly. In the alternative, the tone bursts or segments may all have the same fixed duration, and the periods of silence therebetween may be varied as desired.

It will be readily apparent that various alternative types of circuits and components may be used to perform many of the various functions hereinbefore described. For example, circuitry for determining heart beat, breathing rate, and other physiological phenomena may be substituted for the galvanic skin resistivity circuit 26, as hereinbefore mentioned. Also, it will be apparent that signal F may be used to activate human senses other than hearing.

Many other variations and modifications will readily become apparent to those having experience with circuitry of the type depicted and described herein. Accordingly, it should be clearly understood that the structures and techniques described herein and depicted in the accompanying drawings are illustrative only, and are not intended as limitations on the scope of the present invention.

What is claimed is:

1. A method of presenting educational material to a human subject comprising:
   monitoring the level of concentration of the human subject,
   determining that said subject has attained a preselected level of enhanced capacity for concentration,
   suppressing said determining step once said preselected level has been attained and coincident therewith,
   presenting a preselected program of educational material to said subject.

2. The method according to claim 1 wherein the level of concentration of the subject is monitored by sensing the brain wave frequency of the subject.

3. The method according to claim 1 wherein the level of concentration of the subject is monitored by sensing the skin resistivity of the subject.

4. The method according to claim 1 wherein the level of enhanced capacity for concentration is determined by generating a tone signal of predetermined pitch.

5. The method according to claim 4 wherein the generation of said tone signal is suppressed once said preselected level has been attained.

6. Apparatus for presenting educational material to a human subject comprising:
   means to monitor the level of concentration of the human subject,
   means for determining that said subject has attained a preselected level of enhanced capacity for concentration,
   means for suppressing the operation of said determining means once said preselected level has been attained, and
   means for presenting a preselected program of educational material to said subject when said determining means has been suppressed.

7. Apparatus according to claim 6 wherein said monitor means senses the brain wave frequency of the subject.

8. Apparatus according to claim 6 wherein said monitor means senses the skin resistivity of the subject.

9. Apparatus according to claim 6 wherein said means for determining the preselected level includes means for generating a tone signal of predetermined pitch.

10. Apparatus according to claim 9 wherein the suppressing means suppresses the generation of said tone signal once said preselected level has been attained and coincident therewith activates said program presenting means.

11. Apparatus according to claim 10 wherein said program presenting means comprises a tape player and the like.

* * * * *

UNITED STATES PATENT OFFICE
CERTIFICATE OF CORRECTION

Patent No. 4,008,714　　　　　　　　Dated February 22, 1977

Inventor(s) Jose R. Silva et al.

It is certified that error appears in the above-identified patent and that said Letters Patent are hereby corrected as shown below:

Column 1, line 11, "coending" should read -- copending --.

Column 3, line 54, "difference" should read
　　　　　　-- differences --.

*Signed and Sealed this*

*Twentieth* Day of *December 1977*

[SEAL]

Attest:

RUTH C. MASON　　　　　LUTRELLE F. PARKER
*Attesting Officer*　　*Acting Commissioner of Patents and Trademarks*

UNITED STATES PATENT OFFICE
CERTIFICATE OF CORRECTION

Patent No. 4,008,714                     Dated February 22, 1977

Inventor(s)    JOSE R. SILVA; JOHN M. NARRACE

It is certified that error appears in the above-identified patent and that said Letters Patent are hereby corrected as shown below:

Column 1, Line 59, "mediation" should be "meditation".

Column 1, Line 68, "mediation" should be "meditation".

Column 2, Line 47, "assist" should be "assists".

Column 4, Line 19, "auxilliary" should be "auxiliary".

Column 5, Line 33, "putput" should be "output".

Signed and Sealed this

Seventh Day of March 1978

[SEAL]

Attest:

RUTH C. MASON
Attesting Officer

LUTRELLE F. PARKER
Acting Commissioner of Patents and Trademarks